(12) United States Patent
Portney

(10) Patent No.: US 6,238,433 B1
(45) Date of Patent: May 29, 2001

(54) POSTERIOR/ANTERIOR CHAMBER INTRAOCULAR LENSES AND METHODS OF IMPLANTATION

(75) Inventor: Valdemar Portney, Tustin, CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/166,328

(22) Filed: Oct. 5, 1998

(51) Int. Cl.[7] .......................................... A61F 2/16
(52) U.S. Cl. .......................................... 623/6.54; 623/6.43
(58) Field of Search ............................... 623/6, 6.43, 6.47, 623/6.38, 6.42, 6.46

(56) References Cited

U.S. PATENT DOCUMENTS

| | | |
|---|---|---|
| 3,922,728 | 12/1975 | Krasnov . |
| 4,316,293 | 2/1982 | Bayers . |
| 4,370,760 | 2/1983 | Kelman . |
| 4,403,354 * | 9/1983 | Rainin ......................... 623/6.46 |
| 4,404,694 | 9/1983 | Kelman . |
| 4,476,591 | 10/1984 | Arnott . |
| 4,551,864 | 11/1985 | Akhavi . |
| 4,560,383 | 12/1985 | Leiske . |
| 4,687,484 | 8/1987 | Kaplan . |
| 4,990,159 | 2/1991 | Kraff . |
| 5,047,052 | 9/1991 | Dubroff . |
| 5,071,432 | 12/1991 | Baikoff . |
| 5,147,397 | 9/1992 | Christ et al. . |
| 5,225,858 | 7/1993 | Portney . |
| 5,628,796 | 5/1997 | Suzuki . |
| 5,766,244 | 6/1998 | Binder . |

FOREIGN PATENT DOCUMENTS

| | | |
|---|---|---|
| 0246216 | 5/1987 | (EP) . |
| 0691109 | 7/1994 | (EP) . |
| 97/27825 * | 8/1997 | (WO) ........................... 623/FOR 105 |

* cited by examiner

Primary Examiner—David H. Willse
(74) Attorney, Agent, or Firm—Frank J. Uxa

(57) ABSTRACT

A posterior/anterior chamber intraocular lens for implantation in an eye has an optic and at least one elongated fixation member. The optic has an optical axis. The fixation member has a proximal segment joined to the optic, a distal segment extending away from the optic, and an intermediate segment joining the proximal and distal segments. The intermediate segment has a through-iris portion adapted to extend through the iris of the eye. The distal segment is adapted to be disposed in the posterior chamber of the eye while the proximal segment is adapted to be disposed in the anterior chamber of the eye.

23 Claims, 2 Drawing Sheets

US 6,238,433 B1

POSTERIOR/ANTERIOR CHAMBER INTRAOCULAR LENSES AND METHODS OF IMPLANTATION

BACKGROUND OF THE INVENTION

This invention relates to intraocular lenses (IOL's) and in particular to IOL's that reduce or even eliminate irritation of the ciliary band in the eye and reduce the incidence of papillary block, and, if a natural crystalline lens is present, to reduce the risk of cataract formation.

IOL's are commonly used to modify vision. For example, IOL's are used to replace the natural lens of the eye when warranted by medical conditions. A common practice is to implant an IOL in a region of the eye known as the capsular bag or posterior capsule. However, in this practice, cells from the eye tend to grow on the capsular bag in front of and/or in back of the optical portion of the IOL. This tends to block the optical portion of the IOL and impair vision.

IOL's may be implanted in regions of the eye other than in the capsular bag. Referring now to Prior Art FIG. 1, an anterior IOL (AIOL) 10 is shown implanted in an eye 12. The eye 12 is comprised of a cornea 14 shown to the left and an iris 16 shown in the middle of the eye. It is to be understood that the cornea 14 is at the front of the eye 12. The iris 16 divides the eye 12 into an anterior chamber 18 at the front of the eye and a posterior chamber 20 in back of the iris. The iris 16 also defines the pupil 22, which is an opening in the middle of the iris. In front of the iris 16 is the scleral spur 24. The scleral spur 24 and the iris 18 delimit the ciliary band 26. Behind the iris 16 is the ciliary process 28, from which extends the ciliary muscle 30. The ciliary muscle supports the natural crystalline lens 32 of the eye 12. The iris 16 and the ciliary process 28 define the sulcus 34.

Prior Art FIG. 1 shows the AIOL 10 implanted in the anterior chamber 18 of the eye 12. The AIOL 10 is comprised of an optic 40 that is supported in front of the pupil 22 by loops or haptics 42. The optic 40, for the AIOL 10 and other IOL's described herein, may be considered as including an optical portion for focusing light at or near the retina (not shown) of the eye 12. The haptics 42 extend from the optic 40 and rest in the ciliary band 26. The haptics 42 are designed to minimize compression stress on the optic 40 and inhibit forward vaulting of the optic. If the optic 40 vaults and contacts the cornea 14, an undesirable condition known as endothelium tough may occur. However, this condition may occur from the haptics 42 merely residing in the ciliary band 26.

Referring now to Prior Art FIG. 2, the eye 12 now has a posterior IOL (PIOL) 50 implanted therein. The PIOL 50 is comprised of an optic 52 that is supported behind the pupil 22 by loops or haptics 54. The haptics 54 extend from the optic 52 and rest against the sulcus 34. In terms of inhibiting endothelium tough, the PIOL 50 is superior to the AIOL 10 as the opportunity for any part of the PIOL to contact the cornea 14 is greatly reduced. However, the PIOL 50 has increased opportunity for contacting the natural crystalline lens 32 due to their proximity. Having any object contact the lens 32 is undesirable as it may result in the incidence of papillary block and cataract formation.

It would be advantageous to provide an intraocular lens that reduces, or even minimizes, both the risks of endothelium tough and of papillary block.

SUMMARY OF THE INVENTION

Posterior/anterior chamber intraocular lenses (PACLS) for implantation in an eye have been discovered. The present PACLs have an optic and at least one elongated fixation member, preferably two elongated fixation members. The optic has an optical axis. The fixation member has a proximal segment joined to the optic, a distal segment, for example, extending away from the optic, and an intermediate segment joining the proximal and distal segments. The optic is adapted to be positioned in the anterior chamber, that is anterior of the iris, of the eye, while the distal segment of the fixation member is adapted to be positioned in the posterior chamber, that is posterior of the iris, of the eye. The optic is, thus, spaced apart from the natural crystalline lens of the eye, if such lens is present, and reduces the risk of cataract formation in the natural lens and papillary block. The fixation member, that is the distal segment of the fixation member, being positioned in the posterior chamber reduces the risk of endothelium tough and effectively fixates or fixes the PACL in the eye.

In one embodiment, the intermediate segment of the fixation member has a through-iris portion adapted to extend through the iris of the eye in which the PACL is implanted. For example, a hole may be provided which extends through the iris. The through-iris portion is adapted to extend through the hole. The hole may be an iridectomy opening. The through-iris portion of the fixation member preferably has a longitudinal axis oriented in a direction other than normal to the optical axis. More preferably, the through-iris portion extends generally parallel to the optical axis of the optic.

The through-iris portion may comprise two ends defining a line that is not normal to the optical axis. The line may be generally parallel to the optical axis.

In one embodiment of the invention, the fixation member defines an arc with a discontinuity, preferably at the intermediate segment. The discontinuity preferably extends generally parallel to the optical axis. The arc may extend generally tangentially away from the optic.

The proximal segment of the fixation member preferably is adapted to be disposed in the anterior chamber. This arrangement inhibits the optic from contacting the natural lens of the eye, which can result in papillary block and cataract formation. The distal segment is adapted to be disposed in the posterior chamber of the eye. This arrangement inhibits the distal segment from contacting the cornea and causing endothelium tough. In one very useful embodiment, the distal segment of the fixation member is adapted to be more flexible than the proximal segment or intermediate segment. For example, the distal segment can be made of a more flexible material of construction and/or can have a reduced cross-sectional area relative to one or more of the other segments of the fixation member. Having a fixation member with a relatively more flexible distal segment tends to reduce the movement of the intermediate segment through the iris. Such reduced movement advantageously results in reduced irritation of the iris.

Another aspect of the invention is directed to methods for implanting an intraocular lens in an eye. These methods comprise providing an intraocular lens having a optic and an elongated fixation member which includes a proximal segment joined to the optic, a distal segment, and an intermediate segment joining the proximal and distal segments. The methods include positioning the optic in the anterior chamber of the eye, and positioning the distal segment of the fixation member in the posterior chamber of the eye. The distal segment positioning step includes placing the distal segment against the sulcus of the eye. The positioning of the distal segment may include directing the distal segment through a hole extending through the iris to dispose the intermediate segment of the fixation member in the iris hole. The directing may include rotating the intraocular lens about the optical axis such that the distal segment of the fixation member moves through the iris hole until the intermediate segment is disposed in the iris hole. In one embodiment, the method further comprises performing an iridectomy to form the iris hole.

The iris hole in which the intermediate segment of the fixation member is located may be enlarged relative to a conventional iridectomy hole, which is often on the order of about 0.5 mm in size. For example, the iris hole may be enlarged before or after disposing the intermediate segment in the iris hole. This feature reduces the risk of eye irritation and enhances beneficial fluid flow between the anterior and posterior chambers of the eye. In a particularly useful embodiment, the iris hole in which the intermediate segment of the fixation member is located is positioned close to the outer periphery of the iris than to the inwardly extending terminus of the iris. The outer peripheral portion of the iris moves less than the inner portion of the iris. Placing the iris hole near the outer periphery reduces the amount of movement of the iris relative to the intermediate segment of the fixation member and, thus, advantageously reduces iris irritation.

Each and every feature described herein, and each and every combination of two or more of such features is included with the scope of the present invention provided that the features included in such a combination are not mutually inconsistent.

These and other aspects of the present invention are apparent in the following detained description and claims, particularly when considered in conjunction with the accompanying drawings in which like parts bear like reference numerals.

BRIEF DESCRIPTION OF THE DRAWINGS

Prior Art

Prior Art

DETAILED DESCRIPTION OF THE DRAWINGS

Figure 1:
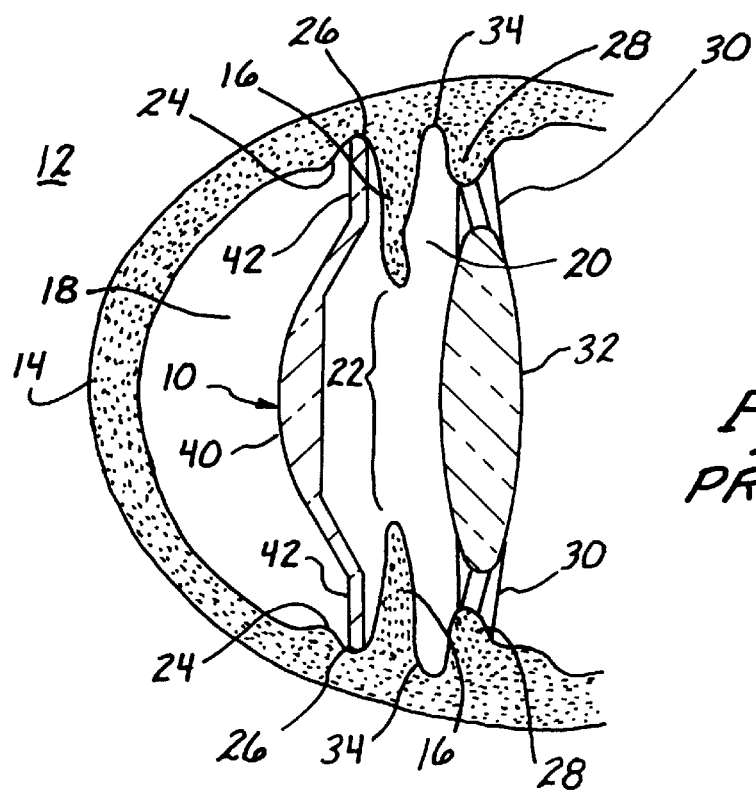
FIG. 1 is a side elevational view of an eye with an anterior intraocular lens implanted therein.
Figure 2:
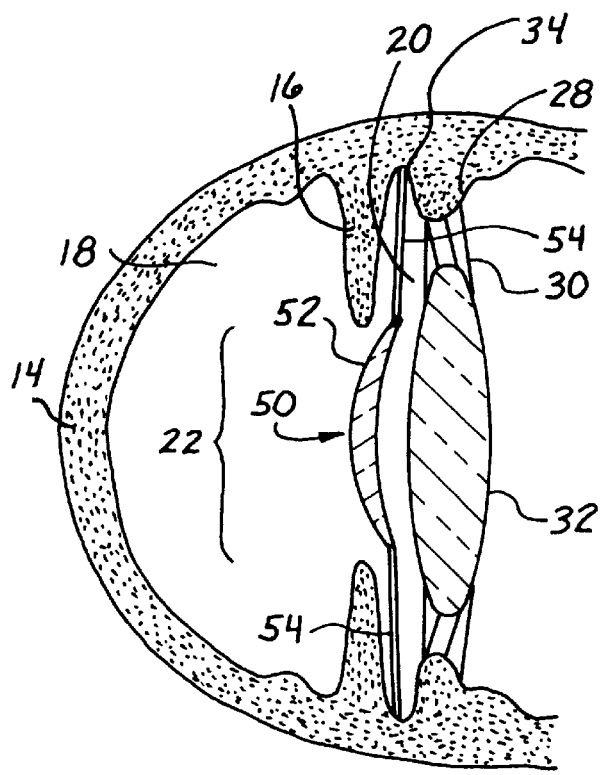
FIG. 2 is a side elevational view of an eye with a posterior intraocular lens implanted therein.
Figure 3:
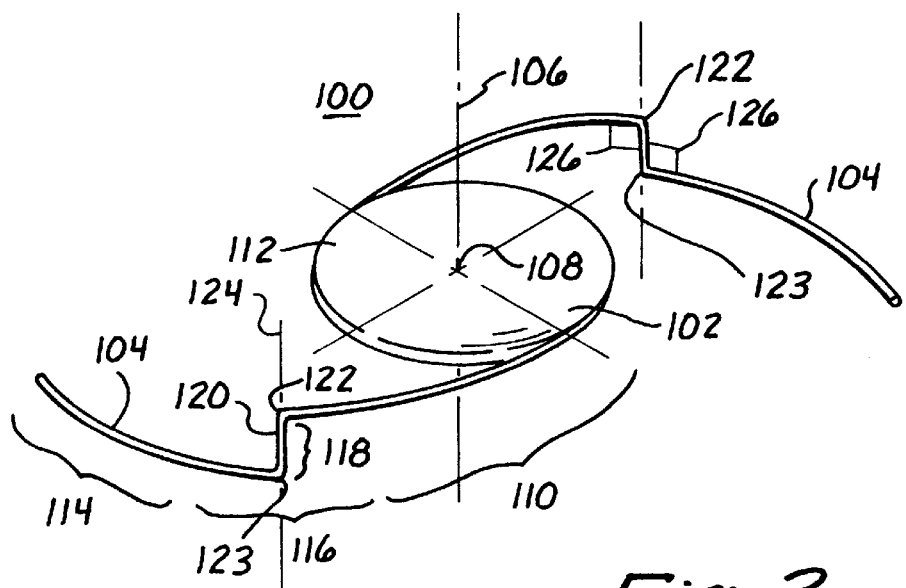
FIG. 3 is a perspective view of an anterior/posterior chamber intraocular lens according to an embodiment of the invention.

Referring now to drawings, FIG. 3 shows an anterior/posterior chamber intraocular lens (PACL) 100 according to an embodiment of the invention. The PACL 100 is comprised of an optic 102 and two opposing elongated fixation members or haptics 104. The optic 102 has an optical axis 106 extending through the center 108 of the optic and is generally normal to the optic. Each haptic 104 has a proximal segment 110 attached to the optic 102 near the periphery 112 of the optic. Each haptic also has a distal segment 114 and an intermediate segment 116 joining the proximal segment 110 and the distal segment. The distal segment 114 preferably is more flexible than the other portions of each of the haptic 104. For example, distal segment 114 can have a reduced cross-sectional area relative to the cross-sectional areas of intermediate segment 116 and proximal segment 110.

Figure 4:
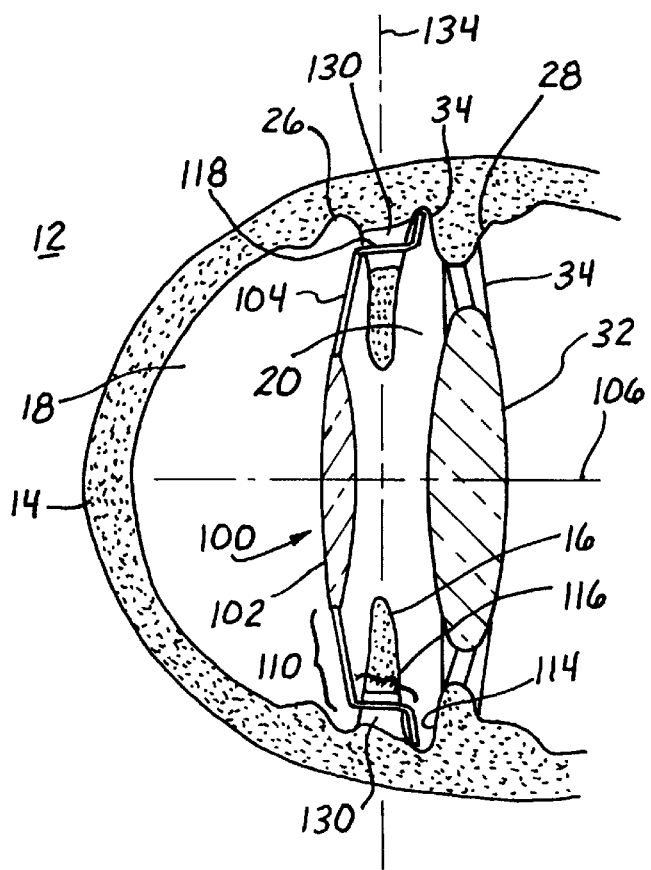
FIG. 4 is a side elevational view of the eye with the anterior/posterior chamber intraocular lens of FIG. 3 implanted therein.

The optic 102 in the shown embodiment is circular in plan and bi-convex (see FIG. 4). Other embodiments of the invention may have other configurations and shapes, such as convex-concave, bi-convex, bi-concave, planar-convex, planar concave, toric, and multifocal, for example, as disclosed in Portney U.S. Pat. No. 5,225,858, which is incorporated herein by reference in its entirety. The optic 102 may by constructed of any commonly employed material or materials used for rigid optics, such as polymethylmethacrylate (PPMA), or commonly used for resiliently deformable or foldable optics, such as silicone polymeric materials, acrylic polymeric materials, hydrogel-forming polymeric materials, such as polyhydroxyethylmethacrylate, and mixtures thereof and the like. Such foldable/deformable optics are particularly advantageous since they may be inserted into the eye through a small incision.

The haptics 104 may be formed integrally with the optic 102 or may be separately attached to the optic.

The haptics 104 may comprise any of a variety of materials which exhibit sufficient supporting strength and resilience, and which are substantially biologically inert in the intended in vivo environment. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like. More preferably, the haptics 104 comprise a polymeric material, in particular selected from polypropylene, PMMA and polyimides, and especially polypropylene. The haptics 104 can be produced using conventional and well known forming techniques. For example, the preferred polymeric haptics can be formed in accordance with known thermoplastic polymer forming techniques, such as by injection molding or by extrusion.

Each haptic 104 defines an arc that extends generally normal to the optical axis 106. Each haptic 104 has a discontinuity or a through-iris portion 118 in the intermediate segment 116. The through-iris portion 118 extends generally parallel to the optical axis 106. Other embodiments of the invention may have other suitable arrangements for the haptics 104 and the through-iris portions 118. In the shown embodiment, the haptics 104 are symmetrical. Other embodiments of the invention may have non-symmetrical haptics. In the shown embodiment of the invention, the haptics 104 extend generally tangentially away from the optic periphery 112. Other embodiments of the invention may have haptics 104 attached to the optic 102 which extend in a non-tangential fashion.

The through-iris portion 118 may extend in any suitable direction other than normal to the optical axis 106. In the shown embodiment of the invention, the through-iris portion 118 includes a straight member 120 extending between two ends 122 and 123, with the two ends defining a line or longitudinal axis 124 that extends generally parallel to the optical axis 106. In other embodiments of the invention, the member 120 between the two ends 122 and 123 may not be straight. Further, the line 124 defined by the two ends 122 and 123 may not be parallel to the optical axis 106. In the shown embodiment of the invention, right angle bends 126 in the haptics 104 occur at ends 122 and 123. Other embodiments of the invention may include other shapes at the ends 122 and 123, which may result in the ends being not as clearly defined, as compared to the shown embodiment.

There may be more than two haptics 104 or only one haptic. In another embodiment of the invention, the haptics 104 may not have a generally arc shape with a discontinuity, but may be of other suitable shapes.

Referring now to FIG. 4, the PACL 100 is shown implanted in the eye 12. Prior to implantation, an iridectomy is performed to form the holes 130 that extend through the iris 16 near the outer periphery of the iris. The iridotomy improves fluid flow between the anterior chamber 18 and the posterior chamber 20. The holes 130 extend through the iris 16 generally parallel to the optical axis 106. Other embodiments of the invention may have the holes 130 extending other than parallel to the optical axis.

The PACL 100 is implanted such that the optic 102 and the proximal segments 110 of the haptics 104 are disposed in the anterior chamber 18. With the optic 102 in the anterior chamber 18, there is a reduced opportunity for the PACL 100 to contact the natural lens 32 and initiate papillary block and cataract formation. However, it should be understood that PACL 100 can be implanted in and function satisfactorily in an eye in which the natural lens has been extracted, e.g., using conventional techniques, or in an eye in which the natural lens has been extracted and replaced by an intraocular lens, e.g., of conventional design, located in the posterior chamber. Further, the PACL 100 is implanted such that the distal segments 114 of haptics 104 are disposed against the sulcus 34, which reduces the incidence of endothelium tough. The through-iris portions 116 may be angled to further reduce cornea 14 contact, and the resulting endothelium tough.

To implant the PACL 100 such that the proximal segments 110 are in the anterior chamber 18 and the distal segments 114 are in the posterior chamber 20, the intermediate segments 116 extend through a plane 134 defined by the iris 16. In the shown embodiment of the invention, each intermediate segment 116 extends through a corresponding hole 130 that extends through the plane 134. The implantation of the PACL 100 does not rely on fixation of the PACL to the iris 16. In a preferred embodiment of the invention, the holes 130 are larger than the diameter of the haptic 104. In a more preferred embodiment of the invention, the openings 130 are approximately 0.5 mm and the haptic diameter is approximately 0.2 mm.

The holes 130 preferably are located near the outer periphery of the iris 16, as shown in FIG. 4. The PACL 100 is inserted into the anterior chamber 18 of the eye 12, for example, using conventional and well known techniques. The distal segments 114 are inserted into the holes 130, respectively. The PACL 100 is then rotated to slide the distal segments 114 through the holes 130 and dispose the intermediate segments 116 in the holes 130. The distal segments 114 contact the sulcus 34 to position the optic 102 such that it focuses light on the retina (not shown).

The distal segments 114 may be made of non-transparent material, such as PMMA with a dye, to facilitate observing the haptic 104 placement behind the iris 16 under proper illumination. In a preferred embodiment of the invention, the remainder of the haptic 104 is made from visually transparent material to minimize cosmetic issues. Post implantation enlargement of one or more of the holes 130 may be performed in case one or more of the haptics 104 touch the iris 16.

The PACL 100 may be implanted to address different refraction deficiencies, such as hyperopia, astigmatism, myopia, and presbyopia.

Other embodiments of the invention may have haptics 104 of other configurations. In an embodiment of the invention, one or more of the haptics 104 may define something other than an arc with a generally perpendicular discontinuity. The haptic 104 may also be adapted to have the intermediate segment 116 extend through an existing hole in the iris 16 or through the pupil 22.

In the shown embodiment of the invention, the intermediate segments 116 serve as springs to minimize compression stress on the optic 102, thus allowing a reduction in optic thickness while reducing the vaulting of the optic. Reducing the optic thickness and minimizing vaulting inhibits the PACL 100 from contacting the cornea 14 and initiating endothelium tough. Further, reducing optic vaulting improves the precision of the implant power calculation.

While the description above refers to particular embodiments of the present invention, it will be understood that many modifications may be made without departing from the spirit thereof. For example, while FIG. 4 shows the PACL 100 implanted in an eye 12 with a natural lens 32, other embodiments of the invention may have the PACL implanted in an eye without a natural lens, or with a replacement lens. Further, aspects of the invention may have combinations of the above described embodiments although these combinations may not be explicitly described.

While this invention has been described with respect to various specific examples and embodiments, it is to be understood that the invention is not limited thereto and that it can be variously practiced within the scope of the following claims.

What is claimed is:

1. An intraocular lens for implantation in an eye having an anterior chamber, an iris and a sulcus located in a posterior chamber, the intraocular lens comprising:

an optic having an optical axis; and two elongated fixation members each comprising a proximal segment joined to the optic and structured and adapted to be disposed in the anterior chamber, a distal segment structured and adapted to be disposed against the sulcus, and an intermediate segment joining the proximal and distal segments, the intermediate segment comprising a through-iris portion having a longitudinal axis oriented substantially parallel to the optical axis and adapted to extend through the iris of the eye in which the intraocular lens is to be implanted.

2. The intraocular lens of claim 1, wherein the through-iris portion is adapted to extend through a hole in the iris.

3. The intraocular lens of claim 1, wherein the through-iris portion is adapted to extend through an iridectomy opening.

4. The intraocular lens of claim 1, wherein the distal segment is more flexible than the intermediate segment or the proximal segment.

5. An intraocular lens for implantation in an eye with an iris, an anterior chamber in front of the iris, and a posterior chamber behind the iris, the intraocular lens comprises:

an optic having an optical axis; and at least one elongated fixation member comprising a proximal segment joined to the optic and adapted to be disposed in the anterior chamber, a distal segment adapted to be disposed in the posterior chamber of the eye, and an intermediate segment joining the proximal and distal segments, the at least one fixation member defines an arc with a discontinuity at the intermediate segment, the arc having a generally convex configuration relative to the optical axis at the proximal segment and the distal segment.

6. The intraocular lens of claim 5, wherein the intermediate segment is adapted to be disposed in a hole extending through the iris of the eye.

7. The intraocular lens of claim 5, wherein the intermediate segment is adapted to extend through an iridectomy opening.

8. The intraocular lens of claim 5, wherein the intermediate segment has a longitudinal axis oriented in a direction other than normal to the optical axis.

9. The intraocular lens of claim 5, wherein the intermediate segment has a longitudinal axis oriented generally parallel to the optical axis.

10. The intraocular lens of claim 5, wherein the discontinuity is oriented substantially parallel to the optical axis.

11. The intraocular lens of claim 5, which includes two of the fixation members.

12. The intraocular lens of claim 5, wherein the distal segment is more flexible than the intermediate segment or the proximal segment.

13. An intraocular lens for implantation in an eye having an anterior chamber, an iris and a sulcus located in a posterior chamber, the intraocular lens comprising:

an optic having an optical axis; and only two elongated fixation members, each fixation member comprising a proximal segment joined to the optic and structured and adapted to be disposed in the anterior chamber, a distal segment extending outwardly from the optic and structured and adapted to be disposed against the sulcus, and an intermediate segment joining the proximal and distal segments, the intermediate segment including a discontinuity oriented substantially parallel to the optical axis.

14. The intraocular lens of claims 13, wherein the distal segment is more flexible than the intermediate segment or the proximal segment.

15. The intraocular lens of claim 13, wherein the fixation member defines an arc with a discontinuity at the intermediate segment.

16. A method for implanting an intraocular lens in an eye with an iris having two holes therethrough, an anterior chamber in front of the iris, a posterior chamber behind the iris, and a sulcus located in the posterior chamber, the method comprising the steps of:

providing an intraocular lens comprising an optic having an optical axis and two elongated fixation members each comprising a proximal segment joined to the optic, a distal segment, and an intermediate segment joining the proximal and distal segments, the intermediate segment comprising a through iris portion having a longitudinal axis oriented substantially parallel to the optical axis;

positioning the optic in the anterior chamber; and positioning the distal segments in the posterior chamber against the sulcus including directing each distal segment through one of the holes in the iris and disposing each through iris portion in one of the holes in the iris.

17. The method of claim 16, further comprising a step of forming the holes in the iris closer to an outer periphery of the iris than to an inwardly extending terminus of the iris, and the directing includes rotating the intraocular lens about the optical axis such that each distal segment moves through one of the holes until the through iris portion of the intermediate segment is disposed in the hole.

18. The method of claim 16, wherein each intermediate segment has a diameter and the hole is larger than the diameter of the intermediate segment.

19. The method of claim 16, which further comprises performing an iridectomy to form the holes in the iris.

20. An intraocular lens for implantation in an eye having an anterior chamber, an iris and a sulcus located in a posterior chamber, the intraocular lens comprising:

an optic having an optical axis; and at least one elongated fixation member comprising a proximal segment joined to the optic and structured and adapted to be disposed in the anterior chamber, a distal segment structured and adapted to be disposed against the sulcus, and an intermediate segment joining the proximal and distal segments, the intermediate segment comprising a through-iris portion having a longitudinal axis oriented substantially parallel to the optical axis and adapted to extend through the iris of the eye in which the intraocular lens is to be implanted, the fixation member defines an arc with a discontinuity at the intermediate segment, the arc having a generally convex configuration relative to the optical axis at the proximal segment and the distal segment.

21. The intraocular lens of claim 20, which includes two of the fixation members.

22. A method for implanting an intraocular lens in an eye with an iris having a hole therethrough, an anterior chamber in front of the iris, and a posterior chamber behind the iris, the method comprising the steps of:

providing an intraocular lens comprising an optic having an optical axis and an elongated fixation member comprising a proximal segment joined to the optic, a distal segment, and an intermediate segment joining the proximal and distal segments, the intermediate segment comprising a through iris portion having a longitudinal axis oriented substantially parallel to the optical axis;

positioning the optic in the anterior chamber;

positioning the distal segment in the posterior chamber including directing the distal segment through the hole in the iris and disposing the through iris portion in the hole in the iris; and enlarging the hole after disposing the through iris portion of the intermediate segment in the hole.

23. A method for implanting an intraocular lens in an eye with an iris having a hole therethrough, an anterior chamber in front of the iris, and a posterior chamber behind the iris, the method comprising the steps of:

providing an intraocular lens comprising an optic having an optical axis and an elongated fixation member comprising a proximal segment joined to the optic, a distal segment, and an intermediate segment joining the proximal and distal segments, the intermediate segment comprising a through iris portion having a longitudinal axis oriented substantially parallel to the optical axis, the elongated fixation member defining an arc with a discontinuity at the intermediate segment, the arc having a generally convex configuration relative to the optical axis at the proximal segment and the distal segment;

positioning the optic in the anterior chamber; and positioning the distal segment in the posterior chamber including directing the distal segment through the hole in the iris and disposing the through iris portion in the hole in the iris.

* * * * *